(12) United States Patent
Sakai et al.

(10) Patent No.: US 8,001,854 B2
(45) Date of Patent: Aug. 23, 2011

(54) ANALYTICAL SAMPLE DRYING METHOD AND DRYING APPARATUS

(75) Inventors: Hiroyuki Sakai, Kokubunji (JP); Shintaro Komatani, Osaka (JP); Yoshihiro Yokota, Takatsuki (JP)

(73) Assignees: Railway Technical Research Institute, Tokyo (JP); HORIBA, Ltd., Kyoto (JP)

( * ) Notice: Subject to any disclaimer, the term of this patent is extended or adjusted under 35 U.S.C. 154(b) by 0 days.

(21) Appl. No.: 12/449,869

(22) PCT Filed: Feb. 29, 2008

(86) PCT No.: PCT/JP2008/000403
§ 371 (c)(1), (2), (4) Date: Oct. 23, 2009

(87) PCT Pub. No.: WO2008/108079
PCT Pub. Date: Sep. 12, 2008

(65) Prior Publication Data
US 2010/0031758 A1    Feb. 11, 2010

(30) Foreign Application Priority Data

| Mar. 2, 2007 | (JP) | 2007-052893 |
| Mar. 28, 2007 | (JP) | 2007-083291 |
| Mar. 30, 2007 | (JP) | 2007-090118 |
| Mar. 30, 2007 | (JP) | 2007-090119 |
| Mar. 30, 2007 | (JP) | 2007-092007 |
| Mar. 30, 2007 | (JP) | 2007-092008 |
| Mar. 30, 2007 | (JP) | 2007-092009 |
| Jun. 14, 2007 | (JP) | 2007-157182 |

(51) Int. Cl.
*G01N 1/00* (2006.01)

(52) U.S. Cl. .......................................................... 73/863

(58) Field of Classification Search .................. None
See application file for complete search history.

(56) References Cited

U.S. PATENT DOCUMENTS
5,704,162 A * 1/1998 Holtkamp, Jr. .................. 47/79
(Continued)

FOREIGN PATENT DOCUMENTS
JP    Y2-03-028360    6/1991
(Continued)

*Primary Examiner* — Robert R Raevis
(74) *Attorney, Agent, or Firm* — Oliff & Berridge, PLC

(57) ABSTRACT

A soil for metal analysis having a high water content of 40% or more is dried up to 20% or less in water content within a short period of time.

A filter paper 5 is laid over an inner bottom surface plate 2 of a nutsche 1. Powder of a super absorbent polymer 6 is uniformly spread (filled) on an upper surface thereof. Further, another filter paper 7 is laid thereon. A soil sample with a high water content is packed on an upper surface thereof, thereupon carrying out predrying to approximately 30% in water content. After that, the predried soil sample is added with ethanol, stirred and received in a receiving pan 38. The receiving pan 38 is arranged in a drying chamber 37. Water is supplied by a syringe 43 to a reaction vessel 42 having been filled with calcium oxide or barium oxide, thereby reacting calcium oxide or barium oxide with water. The receiving pan 38 is heated by a reaction heat generated at that moment, thereupon carrying out postdrying to make the water content 20% or less.

17 Claims, 15 Drawing Sheets

U.S. PATENT DOCUMENTS

| | | | |
|---|---|---|---|
| 6,286,254 B1 * | 9/2001 | Obonai et al. | 47/63 |
| 6,421,959 B1 * | 7/2002 | Van Laere | 47/79 |
| 2008/0038436 A1 * | 2/2008 | Katayama et al. | 426/567 |
| 2008/0244969 A1 * | 10/2008 | Muthiah et al. | 47/48.5 |
| 2010/0075844 A1 * | 3/2010 | Loeker et al. | 502/402 |

FOREIGN PATENT DOCUMENTS

| | | |
|---|---|---|
| JP | B2-08-006350 | 1/1996 |
| JP | A-10-245278 | 9/1998 |
| JP | A-11-051830 | 2/1999 |
| JP | A-2003-299446 | 10/2003 |
| JP | A-2006-138660 | 6/2006 |

* cited by examiner

ANALYTICAL SAMPLE DRYING METHOD AND DRYING APPARATUS

This application is a U.S. National Stage of PCT/JP2008/000403 filed Feb. 29, 2008. The disclosure of the prior applications is hereby incorporated by reference herein in its entirety.

TECHNICAL FIELD

The present invention belongs to the technical field of a drying treatment method and an apparatus for drying treatment for removing an easily vaporized material which includes water contained in an analytical sample used in various chemical analyses such as X-ray fluorescence spectrometry, total reflection X-ray fluorescence spectrometry, infrared spectroscopy, atomic absorption spectrometry, emission spectrometry, gas chromatographic spectrometry, gravimetric analysis, etc.

BACKGROUND ART

In circumstances where a sample is analyzed by using various analytical methods such as X-ray fluorescence spectrometry, total reflection X-ray fluorescence spectrometry, etc., for example, taking X-ray fluorescence spectrometry or total reflection X-ray fluorescence spectrometry as an example, water in a constituent attenuates x-rays thereby reducing x-ray intensity in general. Accordingly, a water content condition of a soil having been collected from a site varies if the soil is analyzed as it is. As a result, there is a problem that a stable measurement value cannot be obtained and thus reliability is poor. Therefore, when a collected soil is used as a sample, attempts, such as those described in Japanese Published Unexamined Patent Application No. 2006-138660, which is incorporated by reference herein in its entirety, have been made to infuse the collected sample with water, mix, dry, and then measure it.

DISCLOSURE OF THE INVENTION

Problems to be Solved by the Invention

The aforementioned conventional method is, however, configured such that the collected sample is infused with water and mixed and then the water is removed by drying. As a drying means in this case, drying is carried out by heating with use of a sheet-shaped or belt-shaped warming body made of heat resistant plastic. However, this method requires a specialized warming body, so that an apparatus itself is upsized and a large amount of power consumption is involved. Thus, there is a problem that a simple and easy drying operation at a collection site cannot be performed and the operation is possible only at well-equipped facilities such as a laboratory. Furthermore, the operation is unsuitable for drying a soil with a high water content where water drips and falls within a short period of time and drying at a collection site has not been attempted. Thus, here are problems to be solved by the present invention.

Means for Solving the Problems

The present invention was made in view of the aforementioned circumstances with the aim of solving these problems. The invention includes a method for drying treatment of an analytical sample, the method comprising the steps of packing the sample into a super absorbent polymer having been spread in a container and drying the sample.

The invention also includes a method for drying treatment of an analytical sample as above, wherein the sample to be dried is a soil for metal analysis with a high water content, and a water content thereof calculated as an amount of water relative to a weight of the soil having been dried is 30% or more.

The invention also includes a method for drying treatment of an analytical sample, which is a method for drying treatment of a soil for metal analysis with a high water content as the analytical sample, the method comprising the steps of carrying out predrying of packing the sample into a super absorbent polymer having been spread in a container and drying the sample, and then carrying out postdrying by heating by use of a heat source, thereby making the water content 20% or less.

The invention also includes a method for drying treatment of an analytical sample as above, wherein the heat source for the postdrying is an electrothermal heater.

The invention also includes a method for drying treatment of an analytical sample as above, wherein the heat source for the postdrying is obtained by condensing light having been emitted from a lamp body by a convex lens.

The invention also includes a method for drying treatment of an analytical sample as above, wherein the heat source for the postdrying is a flame for burning a combustible fuel.

The invention also includes a method for drying treatment of an analytical sample as above, wherein the heat source for the postdrying is a drier with a built-in dry cell.

The invention also includes a method for drying treatment of an analytical sample as above, wherein the heat source for the postdrying is a heat generated when calcium oxide or barium oxide is reacted with water.

The invention also includes a method for drying treatment of an analytical sample as above, wherein the heat source for the postdrying is a heat generated when concentrated sulfuric acid is diluted with water.

The invention also includes a method for drying treatment of an analytical sample as above, wherein the heat source for the postdrying is a heat generated when metal powder is oxidized.

The invention also includes a method for drying treatment of an analytical sample as above, wherein the heat source for the postdrying is a heat generated when alkali metal hydroxide or alkaline earth metal hydroxide is bonded with water and hydrated.

The invention also includes a method for drying treatment of an analytical sample as above, wherein the heat source for the postdrying is a heat generated when a vaporized petroleum combustible is burned in the presence of a catalyst of platinum cotton.

The invention also includes a method for drying treatment of an analytical sample as above, wherein the heat source for the postdrying is a heat generated when charcoal powder of plants having been hardened by kneading is burned.

The invention also includes a method for drying treatment of an analytical sample as above, wherein the heat (thermal) source for the postdrying is a reaction heat generated when a mixture of iron or copper powder and sulfur powder is reacted.

The invention also includes a method for drying treatment of an analytical sample as above, wherein the dried soil is added with volatile alcohol and/or ketone, thereupon carrying out the postdrying.

The invention also includes a method for drying treatment of an analytical sample as above, wherein at least one of a residual component or a vaporized component having been dried is used in analysis.

The invention also includes an apparatus for drying treatment of an analytical sample, including a container and a super absorbent polymer filled in the container, wherein the sample is packed on an upper surface of the super absorbent polymer and dried.

The invention also includes an apparatus for drying treatment of an analytical sample, which is an apparatus for drying treatment of a soil for metal analysis with a high water content as the analytical sample, the apparatus comprising a container, a super absorbent polymer filled in the container, a predrying device packing the soil on an upper surface of the super absorbent polymer and drying the soil to 30% or less in water content, and a postdrying device drying the predried soil to 20% or less in water content by heating by use of a heat source.

The invention also includes an apparatus for drying treatment of an analytical sample as above, wherein the container is a funnel with a ceiling surface opened.

The analytical sample can be dried at an early stage without consuming a large amount of power.

Even a soil having a high water content of 30% or more can simply and easily be dried.

The soil for metal analysis with a high water content can be dried at an early stage by double drying of predrying and postdrying.

Even a soil having a high water content of 30% can be dried simply and easily without using large-scale equipment.

At least one of a residual component or a vaporized component having been dried can be analyzed.

DESCRIPTION OF SYMBOLS

Figure 1:
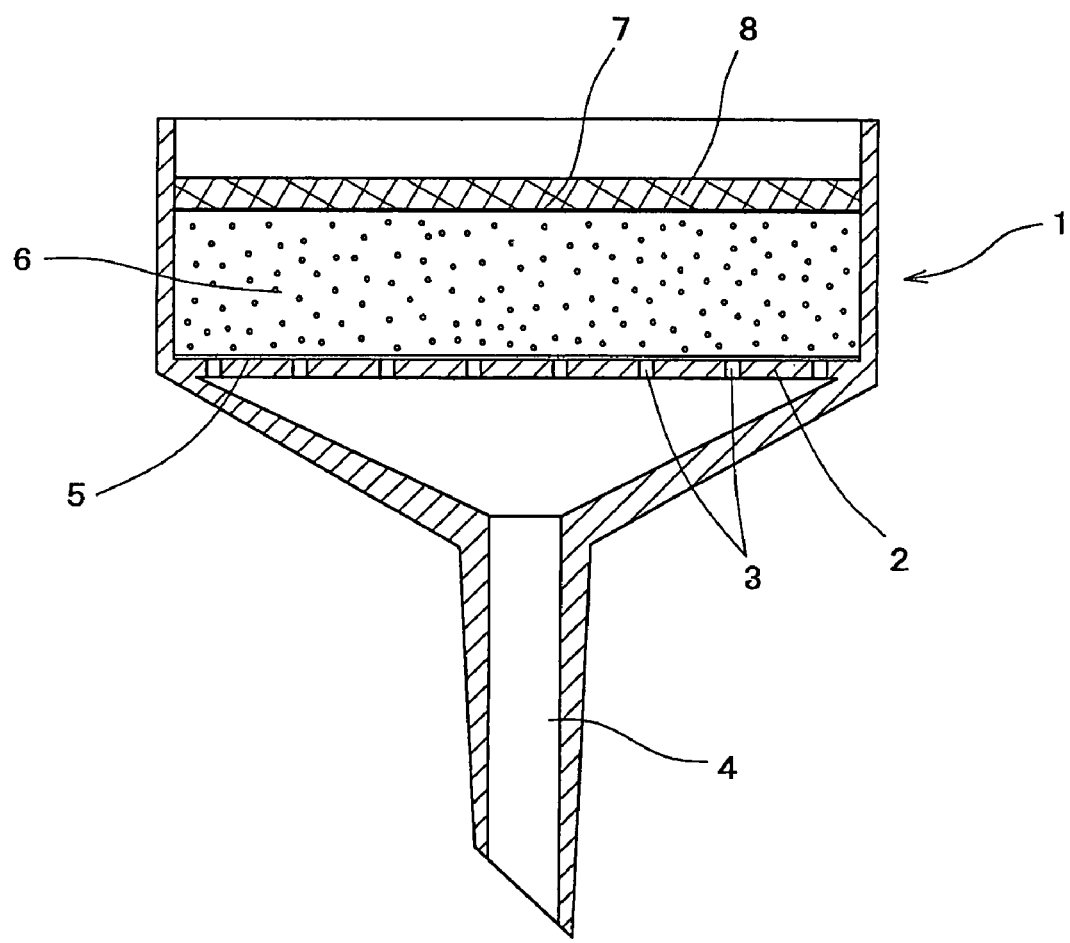
FIG. 1 is a cross sectional view of an apparatus for predrying treatment.

1 Nutsche
6 Super absorbent polymer
8 Test specimen
10 Drier
11 Receiving pan

DETAILED DESCRIPTION

Subsequently, embodiments of the present invention will be described based on the drawings. In the drawings, reference numeral 1 is a nutsche (Büchner funnel) of porcelain or steel covered with a resinous material such as fluororesin on a surface thereof. The nutsche 1 corresponds to a container of a predrying device and has a bottomed cylindrical shape with a ceiling surface opened. A plurality of liquid permeation holes 3 with a small diameter are provided on an inner bottom surface plate 2. A liquid having passed through the liquid permeation holes 3 is configured to be discharged outside via a drain passage 4.

Reference numeral 5 is a lower side filter paper laid over an upper surface of the inner bottom surface plate 2. Powder of a super absorbent polymer 6 is uniformly spread (filled) on an upper surface of the filter paper 5. As the super absorbent polymer 6, there can be adopted cross-linking substances of acrylic polymer moiety and sodium salt which are developed from acrylic acid as a raw material having been manufactured by, for example, vapor-phase oxidation of propylene and also which have superior water absorption and liquid absorption performance relative to wetting materials.

Another filter paper 7 is laid over the upper surface of the super absorbent polymer 6. A test specimen 8 is packed on an upper surface of the filter paper 7 so as to have a predetermined thickness, for example, 5 mm, without leaving any space therebetween, and a surface thereof is formed to be smoothed. The test specimen 8 is a soil to be analyzed by X-ray fluorescence. Herein, kaolin clays having water content of 20, 40, 60 and 80% respectively calculated as an amount of water relative to a weight of a dried soil are adopted in order to check drying conditions. As estimated that water of 300-fold self weight can be absorbed, a spreading (filling) amount of the super absorbent polymer 6 is set to be able to absorb twice a water amount of the water amount contained in respective kaolin clays.

Figure 2:
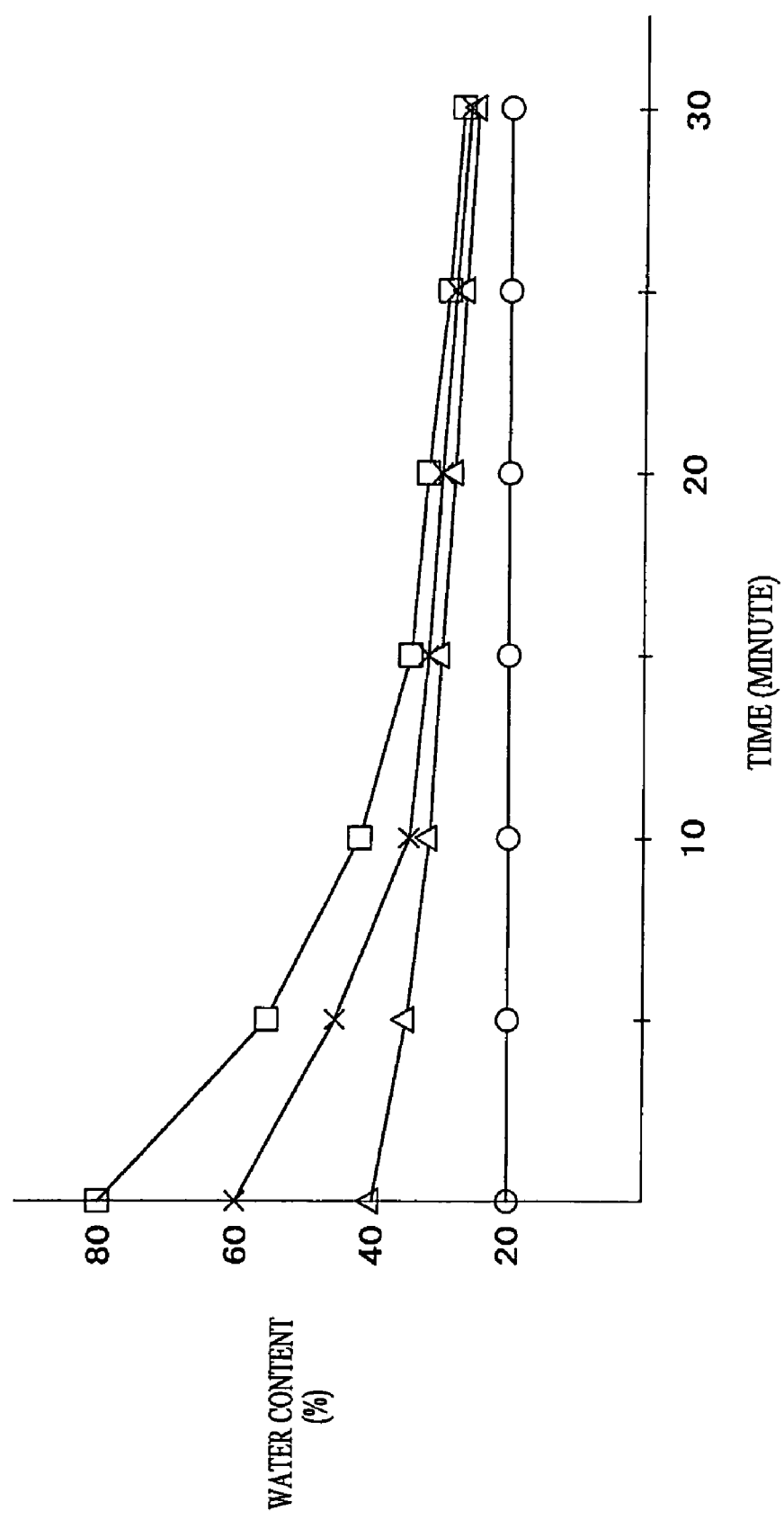
FIG. 2 is a graph chart showing a predrying state.

FIG. 2 illustrates changes in water content of respective kaolin clays. According to the figure, it was recognized that the test specimens 8 with water content of 80 and 60% achieved water content of 40% or less within a short period of time and then the water content gradually decreased, reached approximately 30%, thereafter, the reduction of the water content slackened. On the other hand, the test specimen 8 with a water content of 40% achieved drying to 30% in water content within a short period of time, but the reduction of the water content therebelow slackened. Further, it was recognized that a reduction in water content was slight for the test specimen 8 with a water content of 20%.

From these results, such a predrying treatment that can make a reduction in water content to approximately 30% within a short period of time for a soil with a high water content exceeding 40% becomes possible.

It is noted that a water content is required to be 20% or less, preferably 10% or less in the foregoing various analytical methods such as X-ray fluorescence spectrometry, total reflection X-ray fluorescence spectrometry, etc. Thus, the above drying process shall be considered as a predrying in which a soil with a high water content is dried to 30% in water content at an early stage, and the soil thus predried is further provided with an active drying treatment (postdrying treatment) which makes the water content 20% or less, preferably 10% or less, whereby a test specimen with a targeted water content of 20% or less, preferably 10% or less can be obtained early.

Figure 3:
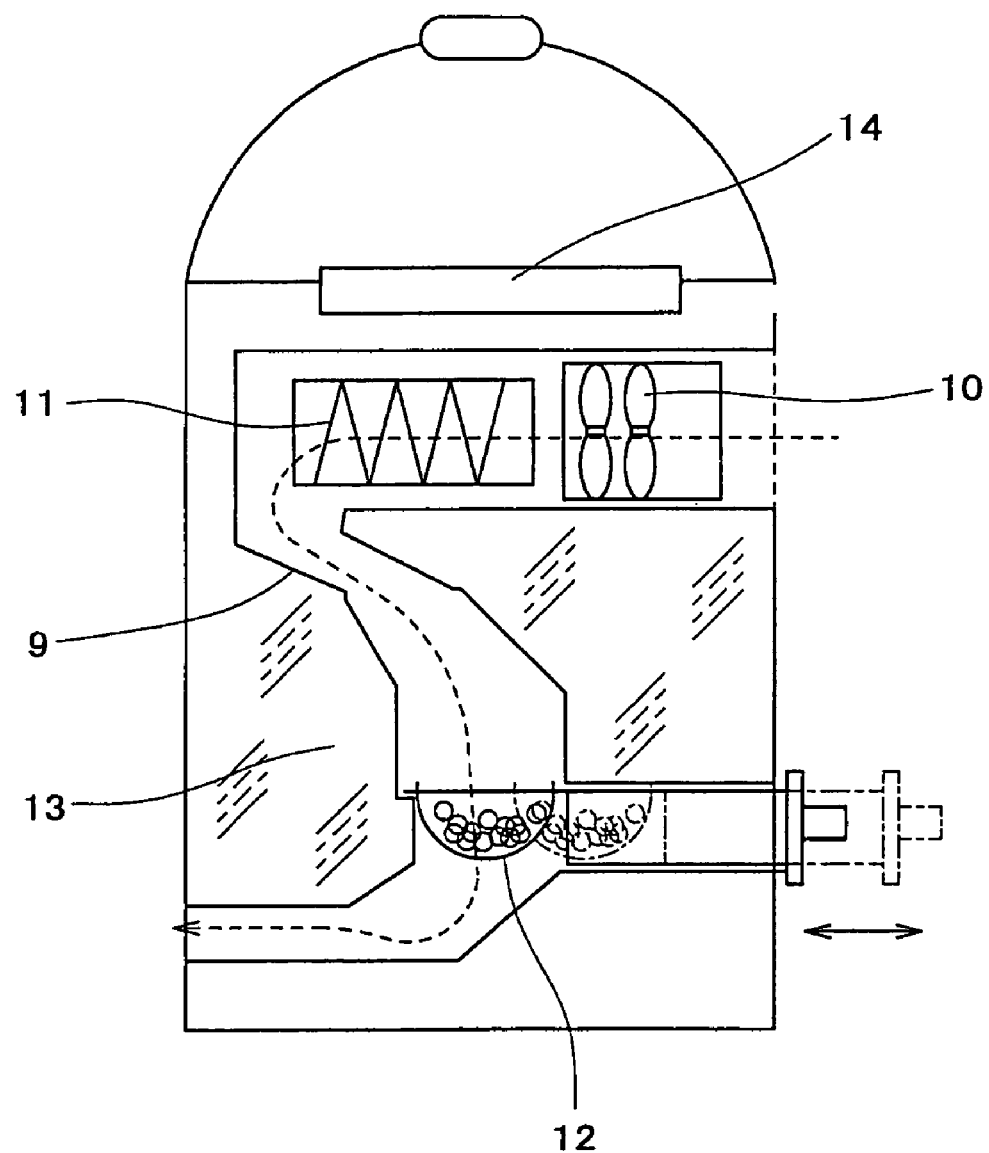
FIG. 3 is a schematic diagram showing a postdrying device of a first embodiment.

Next, examples of a postdrying device will be described based on each embodiment as shown in and after FIG. 3. A postdrying device of a first embodiment as shown in FIG. 3 is a heater-type, and is provided with a fan 10 and a heater 11 at an upstream side of a drying passage 9, and an insertably and extractably pullout sample pan 12 at a downstream side of the drying passage 9. Air heated by the heater 11 is flown to the sample pan 12 as a fan air, thereupon main drying the test specimen having been provided with the predrying treatment. In this case, a heat insulating material 13 is configured to be filled around the drying passage 9, thereby allowing drying efficiency to be increased. It is noted that reference numeral 14 is a panel provided with various instruments such as a temperature indicator of the drying passage 9, a temperature setter of the heater 11, an airflow setter of the fan 10, etc.

By using such a main drying device, the test specimen having been predried to 30% in water content is subject to the thermal active drying treatment, and thus can achieve the targeted water content of 20% or less, preferably 10% or less quickly, and be provided to a to-be-measured sample for the foregoing various analytical methods such as X-ray fluorescence spectrometry, total reflection X-ray fluorescence spectrometry, etc.

Figure 4:
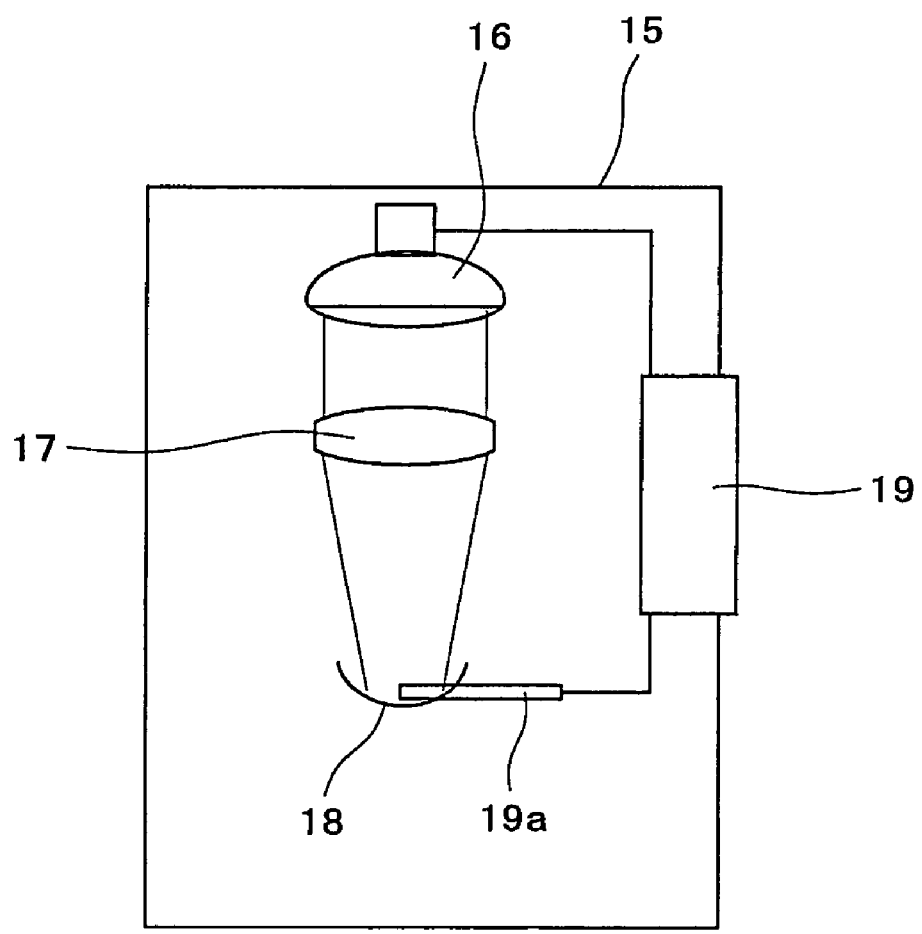
FIG. 4 is a schematic diagram showing a postdrying device of a second embodiment.

The postdrying device further includes a second embodiment as shown in FIG. 4, which is a lamp heating type, provided with a lamp body (for example, a lamp such as halogen lamp, xenon lamp, etc.) 16 as a heating source in a box-shaped drying chamber 15. Light emitted from the lamp body 16 is configured to be further condensed by a convex lens 17. A receiving pan (sample pan) 18 for receiving the aforementioned predried test specimen is provided in the drying chamber 15 and focalized such that the condensed light is irradiated thereon. The aforementioned predried test specimen is heated and dried while placed on the receiving pan 18. In this case, for example, if a heating temperature is set at 80° C., the receiving pan 18 becomes disposable by using a material such as foamed styrol. In this case, a temperature sensor 19a is arranged at the receiving pan 18 and a light amount of the lamp body 16 is adjusted by a temperature regulator 19 based on the detected temperature of the receiving pan 18, thereby allowing a constant temperature state to be maintained.

By using such a main drying device, the aforementioned test specimen having been predried to 30% in water content is subject to the active drying treatment by the condensed light source, and thus can achieve the targeted water content of 20% or less, preferably 10% or less quickly and be provided to a to-be-measured sample for the foregoing various analytical methods such as X-ray fluorescence spectrometry, total reflection X-ray fluorescence spectrometry, etc.

Moreover, in this device, the heat source for the postdrying which makes the predried test specimen 20% or less, preferably 10% or less in water content is a light source having been emitted from the lamp body 16 and then condensed. Thus, there is no need to heat the entire drying box as in drying by hot air, and the receiving pan 18 can locally be heated and can also be heated in an airless state. Consequently, the dried test specimen can be prevented from being dispersed and scattered, as well.

It is noted that a heating temperature can be adjusted by configuring such that the convex lens 17 can move closer to or away from the lamp body 16 or receiving pan 18. Further, the irradiation position can be adjusted by configuring such that the convex lens 17 can move in parallel with the lamp body 16 or receiving pan 18. By this means, early drying can be promoted.

Figure 5:
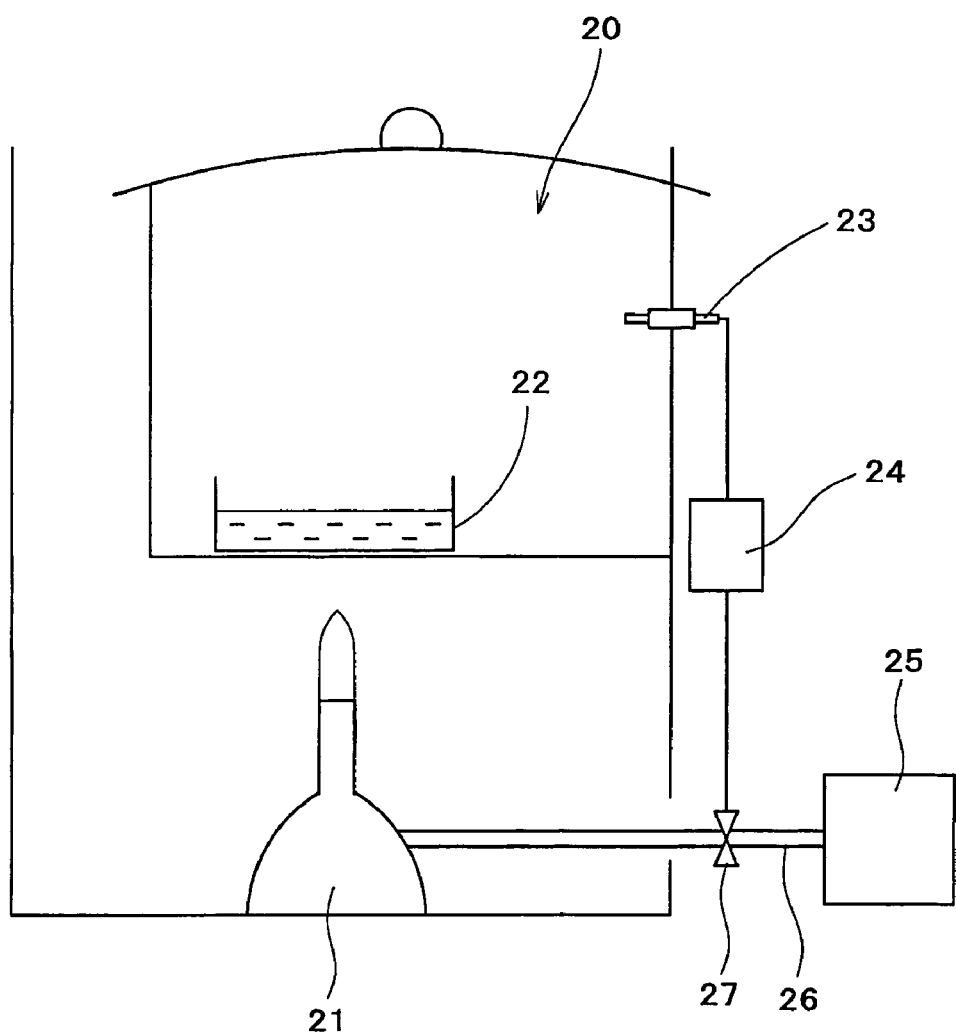
FIG. 5 is a schematic diagram showing a postdrying device of a third embodiment.
Figure 6:
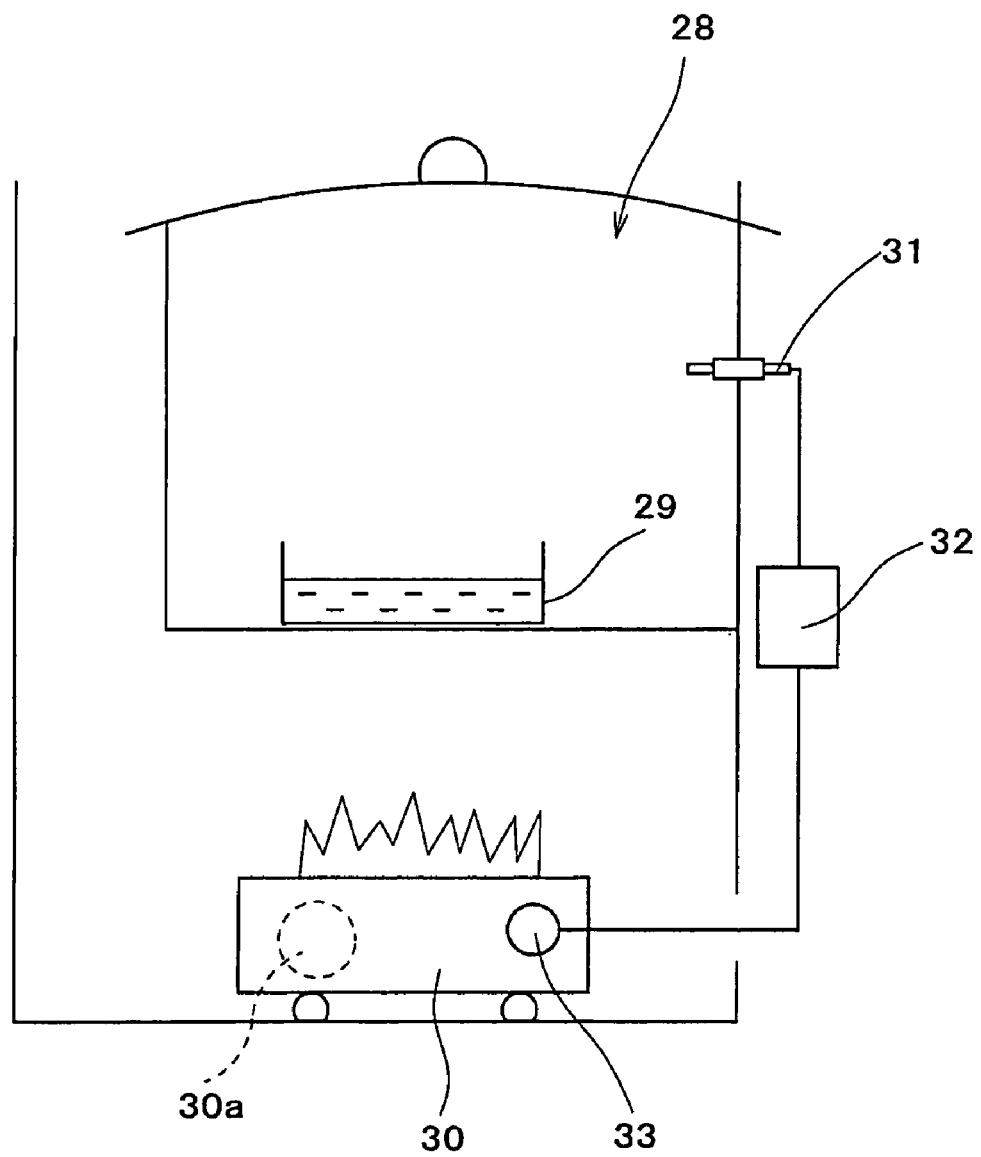
FIG. 6 is a schematic diagram showing a postdrying device of a fourth embodiment.

The postdrying device may further include ones like a third and a fourth embodiment as shown in FIG. 5 and FIG. 6 in which a combustible fuel is burned. First, a postdrying device of the third embodiment as shown in FIG. 5 is a flame burner type and uses a flame burner 21 as a heating source in a box-shaped drying chamber 20. More specifically, it is configured such that a receiving pan (sample pan) 22 for receiving the aforementioned predried test specimen is provided in the drying chamber 20 in such a manner as freely being taken in and out, and the predried test specimen is heated and dried by the flame burner 21 while placed on the receiving pan 22.

The drying chamber 20 is provided with a thermometer 23. A temperature within the drying chamber 20 having been measured by the thermometer 23 is input into a control section 24, which adjusts an opening amount of a fuel supply valve 27 provided in a fuel passage 26 extending from a fuel tank 25 to the flame burner 21, based on the input temperature within the drying chamber 20, thereby adjusting a thermal power of the flame burner 21. Accordingly, a chamber temperature in the drying chamber 20 is set to be kept constant.

By using such a main drying device, the aforementioned test specimen having been predried to 30% in water content is subject to the active drying treatment by the flame burner 21, and thus can achieve the targeted water content of 20% or less, preferably 10% or less quickly, and be provided to a to-be-measured sample for the foregoing various analytical methods such as X-ray fluorescence spectrometry, total reflection X-ray fluorescence spectrometry, etc.

Moreover, in this device, the heating source for the postdrying which makes the predried test specimen 20% or less, preferably 10% or less in water content is the flame burner 21, and accordingly it is sufficient to carry only a combustible gas cylinder as a fuel. Thus, electrical equipment is not required as in a conventional case where a large amount of power consumption is involved, so that drying at the collection site becomes possible.

Furthermore, it is avoidable that water is brought into a boiling state and the sample is mixed therewith and scattered, as in a case where all of the drying is carried out by the flame burner.

A desktop gas stove 30 can also be used as one which carries out the postdrying by flame by burning of combustible gas. More specifically, as in the fourth embodiment as shown in FIG. 6, a drying chamber 28 is provided with a receiving pan (sample pan) 29 for receiving the aforementioned predried test specimen in such a manner as freely being taken in and out, and the predried test specimen is heated and dried by the desktop gas stove 30 while placed on the receiving pan 29. It is noted that reference numeral 30a is a gas cylinder.

The drying chamber 28 is provided with a thermometer 31. A temperature within the drying chamber 28 having been measured by the thermometer 31 is input into a control section 32, which adjusts an opening amount of a thermal power adjusting dial 33 provided in the desktop gas stove 30, based on the input temperature within the drying chamber 28, thereby adjusting a thermal power of the desktop gas stove 30. Accordingly, a chamber temperature in the drying chamber 28 is set to be kept constant.

By using such a main drying device, the aforementioned test specimen having been predried to 30% in water content is subject to the active drying treatment by the desktop gas stove 30, and thus can achieve the targeted water content of 20% or less, preferably 10% or less quickly, and be provided to a to-be-measured sample for the foregoing various analytical methods such as X-ray fluorescence spectrometry, total reflection X-ray fluorescence spectrometry, etc.

Moreover, in this device, the heating source for the postdrying which makes the predried test specimen 20% or less, preferably 10% or less in water content is the desktop gas stove 30, and accordingly it is sufficient to carry only a fuel (gas cylinder). Thus, electrical equipment is not required as in a conventional case where a large amount of power consumption is involved, so that drying at the collection site becomes possible.

Furthermore, it is also avoidable that water is brought into a boiling state and the sample is mixed therewith and scattered, as in a case where all of the drying is carried out by the desktop gas stove 30.

It is a matter of course that the burning of combustible fuel is not restricted to the gas combustion in these embodiments, which can also be carried out by using a heat source obtained by burning liquid fuel such as alcohol, oil, etc., and still further solid fuel.

Figure 7:
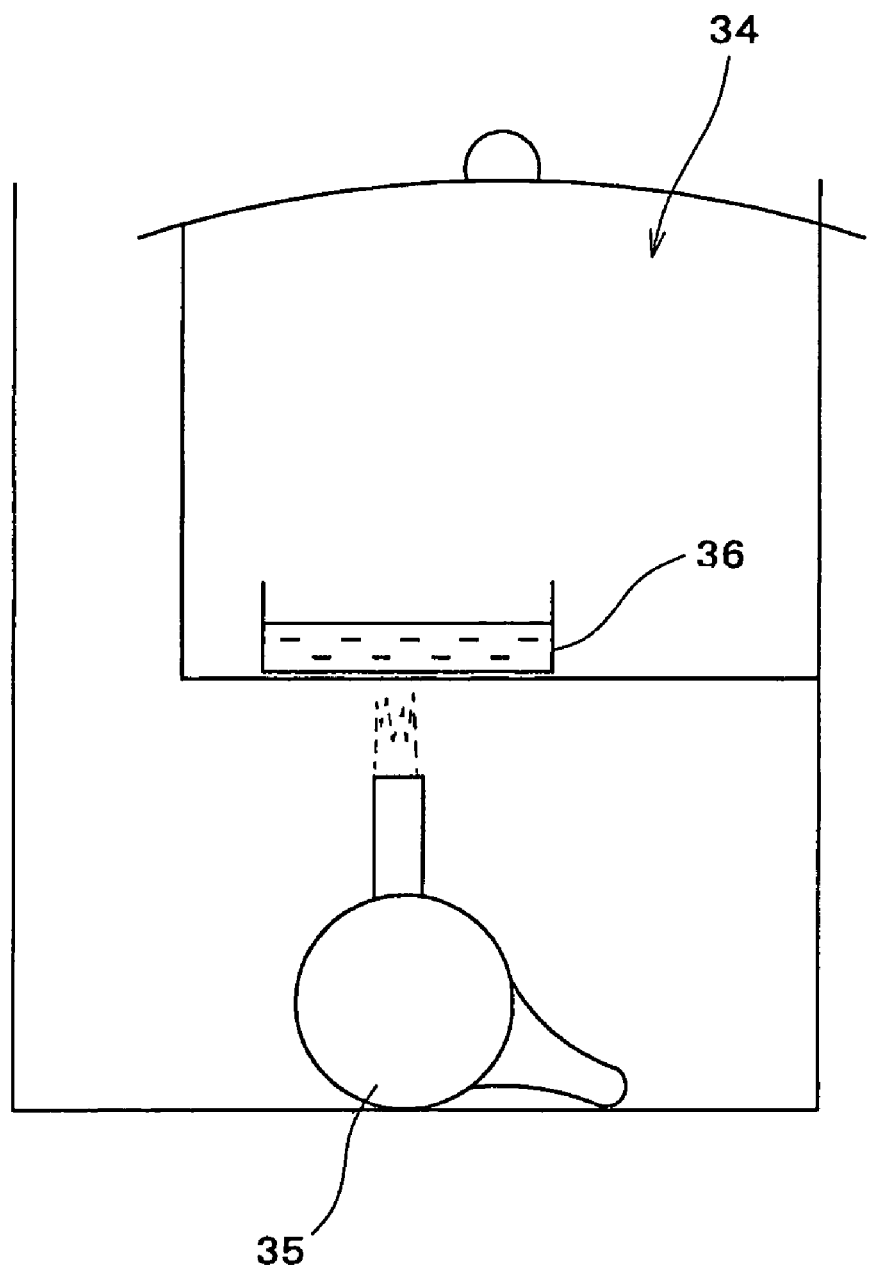
FIG. 7 is a schematic diagram showing a postdrying device of a fifth embodiment.

As the postdrying device, one of a drier type in which a storage cell is housed like a fifth embodiment as shown in FIG. 7 can be adopted. In this device, a drier 35 is used as a heating source in a box-shaped drying chamber 34. More specifically, the drying chamber 34 is provided with a receiving pan (sample pan) 36 for receiving the aforementioned predried test specimen in such a manner as freely being taken in and out. The predried test specimen is heated and dried by applying hot air by the drier 35 from under the receiving pan 36 while placed on the receiving pan 36.

The drier 35 is one which houses the storage cell, which is set to be rechargeable in this embodiment. As a matter of course, however, the present invention can be carried out by using a non-rechargeable storage cell, as well.

By using such a main drying device, the aforementioned test specimen having been predried to 30% in water content is subject to the active drying treatment by hot air from the drier 35, and thus can achieve the targeted water content of 20% or less, preferably 10% or less quickly, and be provided to a to-be-measured sample for the foregoing various analytical methods such as X-ray fluorescence spectrometry, total reflection X-ray fluorescence spectrometry, etc.

Moreover, in this device, the heating source for the postdrying which makes the predried test specimen 20% or less, preferably 10% or less in water content is the drier 35 housed with the storage cell in it, and accordingly heating treatment can be carried out even in a place with no external power supply. Thus, external electrical equipment is not required as in a conventional case where a large amount of power consumption is involved, so that drying at the collection site becomes possible. Furthermore, since the drier 35 is adopted as a heat source only for the postdrying, there is no need to get a large amount of storage cells ready due to heavy consumption of the storage cells as in a case where all of the test specimen is dried by the drier.

It is noted that the drying by the drier 35 is configured to be carried out by applying hot air from under the receiving pan in this embodiment, but can be carried out by applying hot air from directly above the test specimen. In this case, it is conceivable that the test specimen may be scattered. Accordingly, it is preferable that hot air is applied while a woven textile fabric or nonwoven textile fabric with heat resistance is covered. As the woven textile fabric or nonwoven textile fabric, preferably adopted is a metal cloth such as platinum, or one formed from polymer resins with heat resistance such as polycarbonate based resin, polysulfone based resin, etc.

Figure 8A:
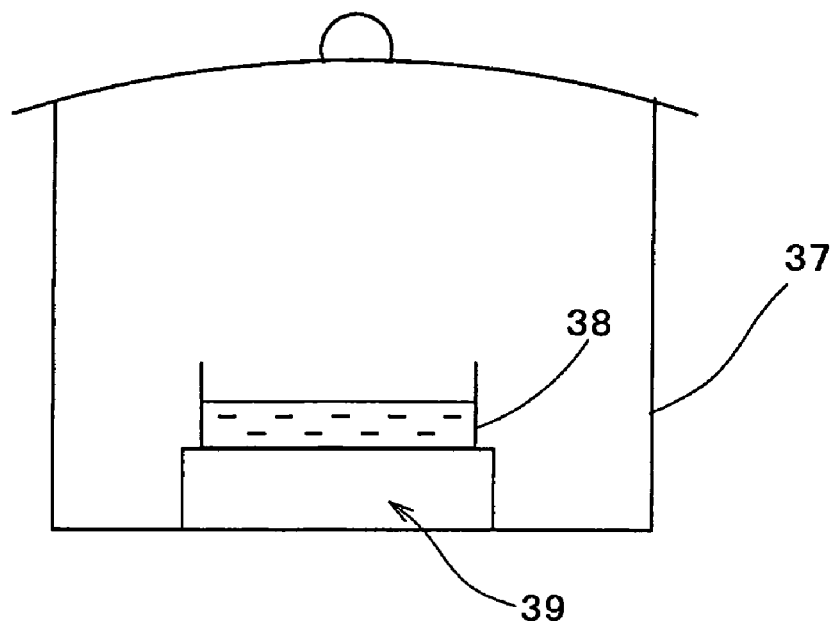
FIG. 8 shows a postdrying device of a sixth embodiment, (A) is a schematic diagram thereof and (B) is a schematic diagram of a reaction vessel.
Figure 8B:
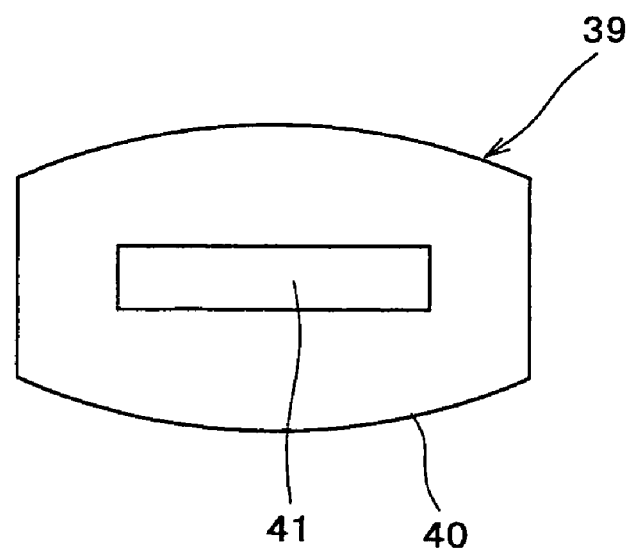
Figure 9:
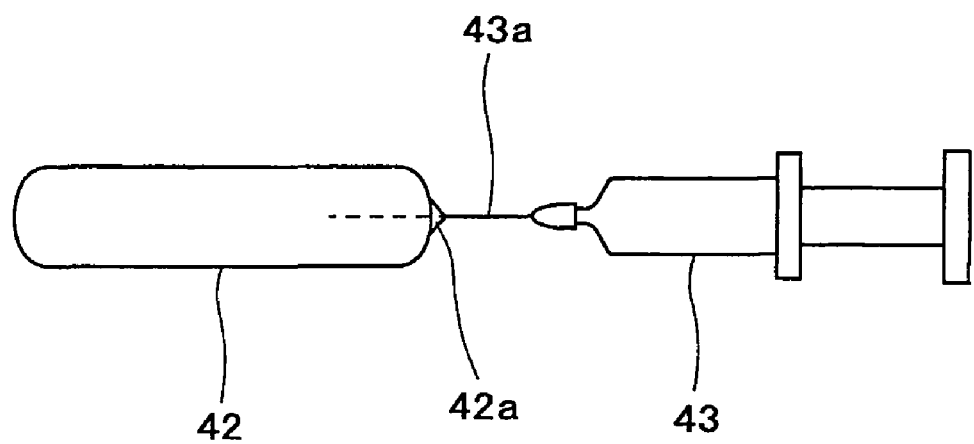
FIG. 9 is a schematic diagram showing a postdrying device of a seventh embodiment.

Still further, the postdrying device may include a sixth and a seventh embodiment as shown in FIG. 8 and FIG. 9. The heat source for the postdrying device in these embodiments is a reaction heat generated when calcium oxide (CaO: burnt lime) is reacted with water to generate calcium hydroxide ($Ca(OH)_2$: hydrated lime). More specifically, a drying chamber 37 is provided with a receiving pan (sample pan) 38 for receiving the aforementioned predried test specimen in such a manner as freely being taken in and out. The predried test specimen is configured to be heated and dried while placed on the receiving pan 38.

Reference numeral 39 is a reaction vessel for hydrated lime. The reaction vessel 39 is composed of an outer container 40 formed of a flexible material and an inner container 41 housed within the outer container 40. The inner container 41 is formed of such a material that is broken by forcibly press-bending the outer container 40, for example, a thin-walled rigid plastic or glass. Powder of calcium oxide is stored in the outer container 40, and water is filled in the inner container 41. At the time of postdrying, if the outer container 40 is press-bent to break the inner container 41, the water is leaked out into the outer container 40, whereupon calcium oxide and water react with each other and a chemical reaction of generating calcium hydroxide proceeds. A reaction heat generated at that moment becomes a heat source for the postdrying. Therefore, the outer container 40 is well kneaded to mix water and calcium oxide uniformly after the inner container 41 is broken. After that, the outer container 40 is placed on the floor of the drying chamber 37, and the receiving pan 38 is placed thereon, thereby allowing for carrying-out of the postdrying.

By using such a main drying device, the aforementioned test specimen having been predried to 30% in water content is subject to the active drying treatment by the heat of reaction between calcium oxide and water, and thus can achieve the targeted water content of 20% or less, preferably 10% or less quickly, and be provided to a to-be-measured sample for the foregoing various analytical methods such as X-ray fluorescence spectrometry, total reflection X-ray fluorescence spectrometry, etc.

Moreover, in this device, the heating source for the postdrying which makes the predried test specimen 20% or less, preferably 10% or less in water content is the reaction heat generated by reacting calcium oxide with water, and accordingly heating treatment can be carried out even in a place with no external power supply. Thus, electrical equipment is not required as in a conventional case where a large amount of power consumption is involved, so that drying at the collection site becomes possible.

It is noted that the drying by the reaction heat generated by reacting calcium oxide with water is configured to be carried out by putting the reaction vessel 40 under the receiving pan 38 in the above seventh embodiment, but can be carried out by placing the reaction vessel 40 from above onto the test specimen, as well (heating from both above and under is also possible). In this case, it is preferable that a woven textile fabric or nonwoven textile fabric with heat resistance is laid over the test specimen so that the test specimen does not contact with the reaction vessel 40 directly. As the woven textile fabric or nonwoven textile fabric, preferably adopted is a metal cloth such as platinum, or one formed from polymer resins with heat resistance such as polycarbonate based resin, polysulfone based resin, etc.

On the other hand, a substance which is reacted with water and generates heat includes barium oxide (BaO). The postdrying of the present invention can be carried out even by using this heat source in the same manner as the case of reacting calcium oxide with water. When calcium oxide or barium oxide is reacted with water, calcium oxide or barium oxide and the inner container having been filled with water may be enclosed in the outer container. However, further, as in the seventh embodiment as shown in FIG. 9, the present invention can be carried out in such a manner that the reaction vessel 42 having been filled with calcium oxide or barium oxide is prepared, and a needle 43a of a water absorbed syringe (injector) 43 is inserted into the reaction vessel 42 to fill the reaction vessel 42 with water. In this case, preferably, the reaction vessel 42 is provided with a thick-walled portion 42a, into which the needle 43a is inserted, thereby avoiding leakage of the reaction liquid from the vessel.

Figure 10A:
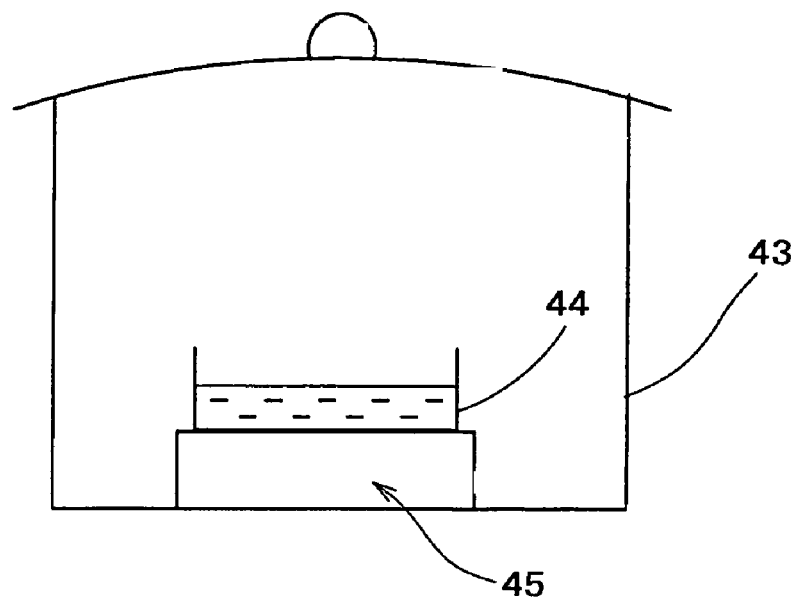
FIG. 10 shows a postdrying device of an eighth embodiment, (A) is a schematic diagram thereof and (B) is a schematic diagram of a dilution vessel.
Figure 10B:
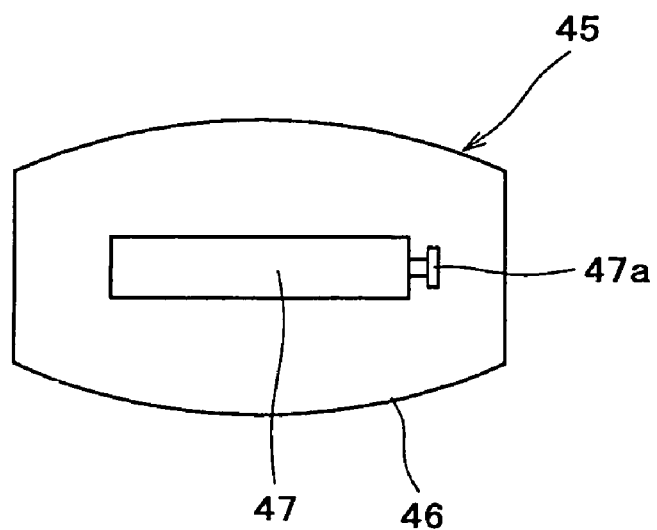

Furthermore, the postdrying device may include an eighth embodiment as shown in FIG. 10, wherein heat generated when concentrated sulfuric acid is diluted with water is used as a heat source. More specifically, a drying chamber 43 is provided with a receiving pan (sample pan) 44 for receiving the aforementioned predried test specimen in such a manner as freely being taken in and out. The predried test specimen is heated and dried while placed on the receiving pan 44.

Reference numeral 45 is a dilution vessel, which is composed of an outer container 46 formed of a flexible material and an inner container 47 housed within the outer container 46. The inner container 47 is provided with a neck portion 47a which is broken, for example, by being pulled or bent. Water is stored in the outer container 46, and concentrated sulfuric acid is filled in the inner container 47. In this case, the amount of water stored in the outer container 46 is an amount that allows sufficient clearance to squeeze and push in the outer container 46 by fingers so as to pinch and then pull or bend the neck portion 47a.

At the time of postdrying, when the outer container 46 is squeezed by fingers to break the neck portion 47a of the inner container 47, the concentrated sulfuric acid is leaked out inside the outer container 46, thereby being diluted with water. A reaction heat generated at that moment becomes a heat source for the postdrying. In this case, the outer container 46 is left to stand on the floor of the drying chamber 43 with the neck portion 47a broken in order to avoid a rapid dilution of the concentrated sulfuric acid, and the receiving pan 44 is placed thereon, thereby carrying out the postdrying. The concentrated sulfuric acid is taken out little by little from the inner container by sometimes pushing the outer container by fingers or the like, whereby heat generation by the dilution can be controlled.

It is noted that the device as shown in FIG. 9 can be adopted when a dilution heat of the concentrated sulfuric acid is used. In this case, the present invention can be carried out by filling concentrated sulfuric acid in a drying vessel and supplying water little by little into a dilution vessel by a syringe.

By using such a main drying device, the aforementioned test specimen having been predried to 30% in water content is subject to the active drying treatment by the heat generated when the concentrated sulfuric acid is diluted with water, and thus can achieve the targeted water content of 20% or less, preferably 10% or less quickly, and be provided to a to-be-measured sample for the foregoing various analytical methods such as X-ray fluorescence spectrometry, total reflection X-ray fluorescence spectrometry, etc.

Moreover, in this device, the heating source for the postdrying which makes the predried test specimen 20% or less, preferably 10% or less in water content is the heat generated at the time of diluting the concentrated sulfuric acid with water, and accordingly heating treatment can be carried out even in a place with no external power supply. Thus, electrical equipment is not required as in a conventional case where a large amount of power consumption is involved, so that drying at the collection site becomes possible.

It is noted that the drying by the heat generated when the concentrated sulfuric acid is diluted with water is configured to be carried out by putting the drying vessel 42 under the receiving pan in this embodiment, but can be carried out by placing the drying vessel 42 from above onto the test specimen, as well (heating from both above and under is also possible). In this case, it is preferable that a woven textile fabric or nonwoven textile fabric with heat resistance is laid over the test specimen so that the test specimen does not contact with the dilution vessel 45 directly. As the woven textile fabric or nonwoven textile fabric, preferably adopted is a metal cloth such as platinum, or one formed from polymer resins with heat resistance such as polycarbonate based resin, polysulfone based resin, etc.

Figure 11:
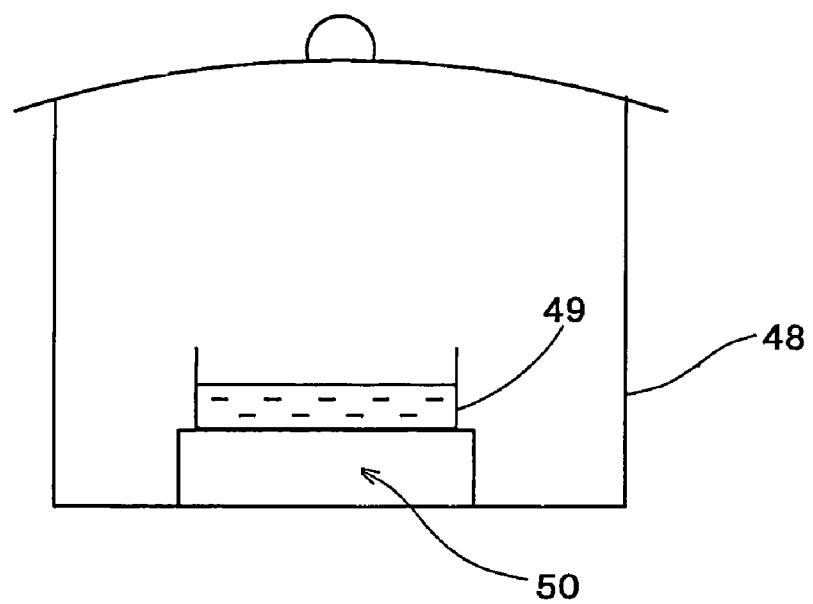
FIG. 11 is a schematic diagram showing a postdrying device of a ninth embodiment.

Still further, the postdrying device includes a ninth embodiment as shown in FIG. 11, wherein powder of metals such as iron, magnesium, aluminum, etc., is more likely to experience an oxidation reaction by reacting with oxygen in air to oxidize, and oxidation heat generated at that moment is used as a heat source. More specifically, a drying chamber 48 is provided with a receiving pan (sample pan) 49 for receiving the aforementioned predried test specimen in such a manner as freely being taken in and out, and the predried test specimen is heated and dried while placed on the receiving pan 49.

Reference numeral 50 is an oxidation vessel (bag) and is formed from a breathable material. Powder of iron (iron powder) is filled in the oxidation vessel 50. In this device, activated carbon having been absorbed with a saline solution as a water-holding agent is filled and mixed in order to control an oxidation rate of the iron powder. This filling amount can control the oxidation rate of the iron powder, that is, a rate of oxidation reaction, thereby regulating a generation amount of oxidation heat.

The oxidation vessel 50 is kept within a hermetically sealed container in order to prevent progression of iron powder oxidation, and is taken out of the hermetically sealed container to be exposed to air at a postdrying stage. By this, air is entered into the oxidation vessel 50, oxidation of iron powder proceeds, and heat is generated. Herein, the oxidation vessel 50 is left to stand on the floor of the drying chamber 48, and the receiving pan 49 is placed thereon to carry out the postdrying. Further, the postdrying can also be carried out by placing the oxidation vessel 50 on the upper surface of the receiving pan 49 according to need.

By using such a main drying device, the aforementioned test specimen having been predried to 30% in water content is subject to the active drying treatment by the oxidation heat generated when the metal powder is oxidized, and thus can achieve the targeted water content of 20% or less, preferably 10% or less quickly, and be provided to a to-be-measured sample for the foregoing various analytical methods such as X-ray fluorescence spectrometry, total reflection X-ray fluorescence spectrometry, etc.

Moreover, in this device, the heating source for the postdrying which makes the predried test specimen 20% or less, preferably 10% or less in water content is the oxidation heat generated when the metal powder is oxidized, and accordingly heating treatment can be carried out even in a place with no external power supply. Thus, electrical equipment is not required as in a conventional case where a large amount of power consumption is involved, so that drying at the collection site becomes possible.

It is noted that the drying by the reaction heat generated by oxidation of the metal powder is configured to be carried out by putting the oxidation vessel 50 under the receiving pan in this embodiment, but can be carried out by placing the oxidation vessel 50 from above onto the test specimen, as well (heating from both above and under is also possible). In this case, it is preferable that a woven textile fabric or nonwoven textile fabric with heat resistance is laid over the test specimen so that the test specimen does not contact with the oxidation vessel 50 directly. As the woven textile fabric or nonwoven textile fabric, preferably adopted is a metal cloth such as platinum, or one formed from polymer resins with heat resistance such as polycarbonate based resin, polysulfone based resin, etc.

Figure 12:
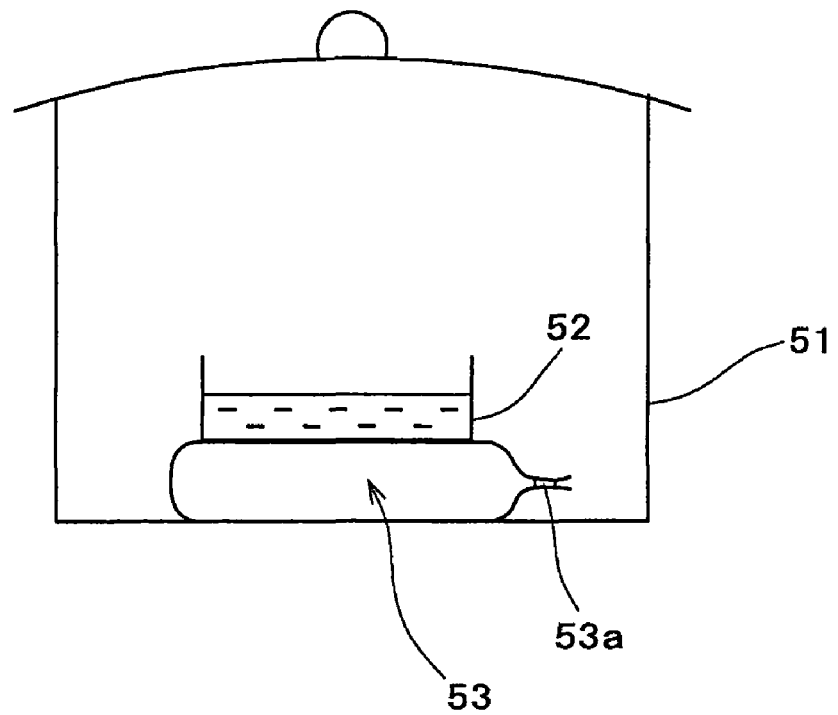
FIG. 12 is a schematic diagram showing a postdrying device of a tenth embodiment.

Still further, the postdrying device may include a tenth embodiment as shown in FIG. 12, which uses hydration heat generated when alkali metal hydroxide as represented by lithium hydroxide (LiOH), sodium hydroxide (NaOH) and potassium hydroxide (KOH), or alkaline earth metal hydroxide as represented by magnesium hydroxide ($Mg(OH)_2$) and calcium hydroxide ($Ca(OH)_2$) is bonded with water and hydrated. More specifically, a drying chamber 51 is provided with a receiving pan (sample pan) 52 for receiving the aforementioned predried test specimen in such a manner as freely being taken in and out, and the predried test specimen is heated and dried while placed on the receiving pan 52.

Reference numeral 53 is a heat generation vessel (bag), and is formed from a flexible and non-breathable material. Particulate sodium hydroxide is filled in the heat generation vessel 53 in an atmosphere of inert gas such as nitrogen gas, and contact with water is blocked. The heat generation vessel 53 is provided with a zippered opening 53a capable of being openably and closably sealed. When the opening 53a is opened, poured with water and sealed, and then the heat generation vessel 53 is well kneaded, sodium hydroxide and water is bonded and well hydrated. The heat generation vessel 53 is left to stand on the floor of the drying chamber 51, and the receiving pan 52 is placed thereon to carry out the postdrying. The heat generation vessel 53 can also be placed on the upper surface of the receiving pan 52 to carry out the postdrying according to need (drying from both above and under is also possible if necessary). In this case, an amount of hydration heat generated varies according to an amount of water to be added relative to sodium hydroxide. It is preferable to add heated water (hot water) in order to ensure a heating temperature.

By using such a main drying device, the aforementioned test specimen having been predried to 30% in water content is subject to the active drying treatment by the hydration heat generated when sodium hydroxide is hydrated with water, and thus can achieve the targeted water content of 20% or less, preferably 10% or less quickly, and be provided to a to-be-measured sample for the foregoing various analytical methods such as X-ray fluorescence spectrometry, total reflection X-ray fluorescence spectrometry, etc.

Moreover, in this device, the heating source for the postdrying which makes the predried test specimen 20% or less, preferably 10% or less in water content is the hydration heat generated when alkali metal hydroxide or alkaline earth metal hydroxide is bonded with water and hydrated, and accordingly heating treatment can be carried out even in a place with no external power supply. Thus, electrical equipment is not required as in a conventional case where a large amount of power consumption is involved, so that drying at the collection site becomes possible.

Figure 13:
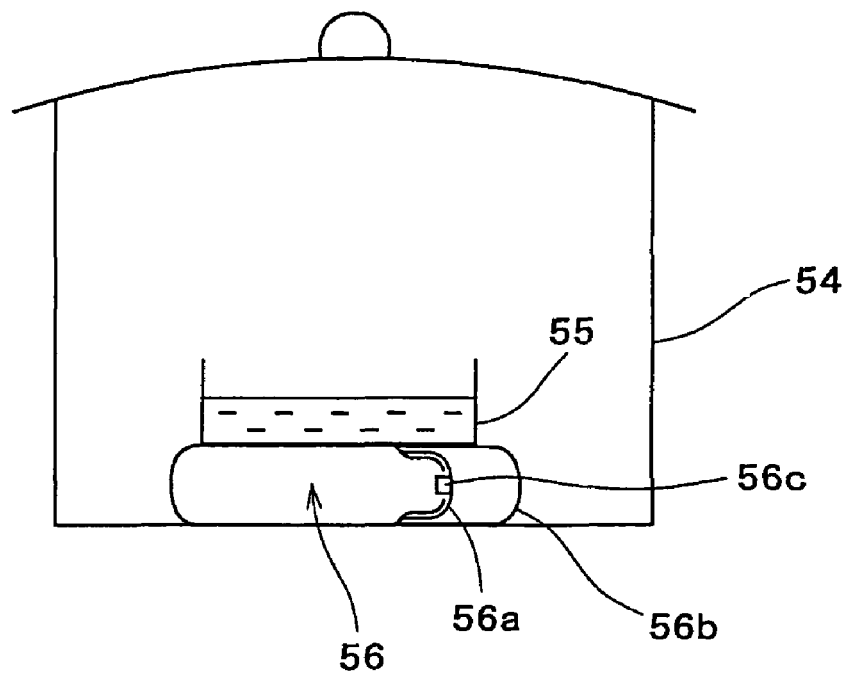
FIG. 13 a schematic diagram showing a postdrying device of an eleventh embodiment.
Figure 14:
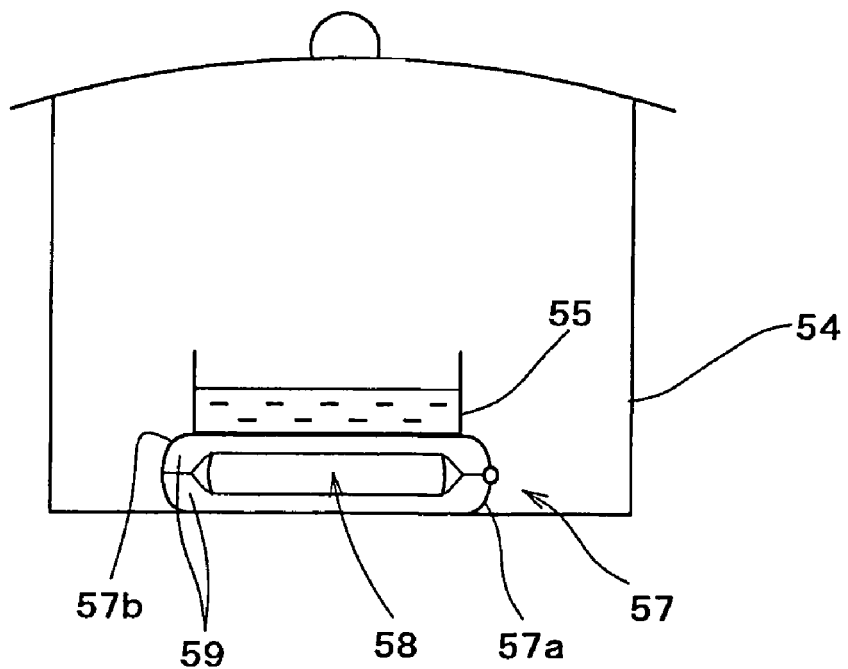
FIG. 14 is a schematic diagram showing a postdrying device of a twelfth embodiment.

Furthermore, the postdrying device may include an eleventh and a twelfth embodiment as shown in FIG. 13 and FIG. 14, which use combustion heat generated when a vaporized petroleum combustible (as represented by benzine) is burned in the presence of a catalyst of platinum cotton, or combustion heat generated when charcoal powder of plants having been hardened by kneading is burned.

More specifically, the eleventh embodiment as shown in FIG. 13 is provided with a receiving pan (sample pan) 55 for receiving the aforementioned predried test specimen in a drying chamber 54 in such a manner as freely being taken in and out. The predried test specimen is heated and dried while placed on the receiving pan 55.

Reference numeral 56 is a heat generation vessel for burning a petroleum combustible and generating heat, and is formed from a metal material. Glass wool with heat resistance is filled in the heat generation vessel 56, and the petroleum combustible as represented by benzine is configured to be supplied and filled in the vessel 56 by removing a cap 56a from the vessel 56. The cap 56a is provided with a platinum cotton (platinum wire netting) 56c and configured to be covered by a covering body 56b which is breathable and capable of supplying oxygen in air to the cap 56a region. The vessel 56 is heated by combustion heat generated when combustible gas into which the petroleum combustible having been filled within the vessel 56 is vaporized is burned under the platinum cotton as a catalyst. The vessel 56 is left to stand on the floor of the drying chamber 54, and the receiving pan 55 is placed thereon to carry out the postdrying. The heat generation vessel 56 can also be placed on the upper surface of the receiving pan 55 to carry out the postdrying according to need (drying from both above and under is also possible if necessary).

By using such a main drying device, the aforementioned test specimen having been predried to 30% in water content is subject to the active drying treatment by the combustion heat generated when the petroleum combustible is slowly burned under the platinum cotton 56c as a catalyst, and thus can achieve the targeted water content of 20% or less, preferably 10% or less quickly, and be provided to a to-be-measured sample for the foregoing various analytical methods such as X-ray fluorescence spectrometry, total reflection X-ray fluorescence spectrometry, etc.

Moreover, in this device, the heating source for the postdrying which makes the predried test specimen 20% or less, preferably 10% or less in water content is the combustion heat generated when the petroleum combustible is slowly burned under the platinum cotton as a catalyst, and accordingly heating treatment can be carried out even in a place with no external power supply. Thus, electrical equipment is not required as in a conventional case where a large amount of power consumption is involved, so that drying at the collection site becomes possible.

Additionally, in the twelfth embodiment as shown in FIG. 14, reference numeral 57 is a heat generation vessel with air permeability for burning a combustible 58 which is charcoal powder of plants having been hardened by kneading, and making generated combustion heat into a heat source. The vessel 57 is composed of a vessel body 57a and an openable and closable cover body 57b. Inside of the vessel body 57a and the cover body 57b, there are provided rugs 59 formed by weaving glass wool with heat resistance. The vessel 57 supports and burns the combustible 58 in such a manner as sandwiching it by the rugs 59. This vessel can also be adopted as a heat source for the postdrying in the same manner as above.

Figure 15:
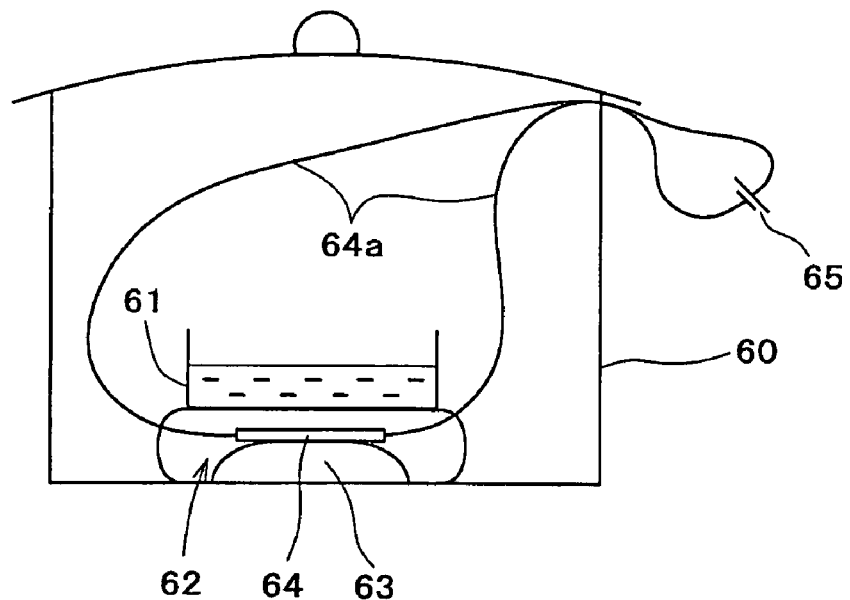
FIG. 15 is a schematic diagram showing a postdrying device of a thirteenth embodiment.

The postdrying device may include a thirteenth embodiment as shown in FIG. 15, in which a reaction heat generated when a mixture of iron or copper powder and sulfur powder is reacted to generate iron sulfide or copper sulfide is used as a heat source. On the other hand, the reaction by only those reaction components is close to an explosion, and thus, powder of potassium silicate ($K_2SiO_3$) is added as a reaction control (inhibition) agent, whereby the reaction is set to proceed gradually.

More specifically, a drying chamber 60 is provided with a receiving pan (sample pan) 61 for receiving the aforementioned predried test specimen in such a manner as freely being taken in and out. The predried test specimen is heated and dried while placed on the receiving pan 61.

Reference numeral 62 is a heat generation vessel for reacting a powder mixture of iron or copper and sulfur and generating heat. The heat generation vessel 62 is a hermetically sealed type. The powder mixture 63 is filled in the heat generation vessel 62 together with an electric heating body 64 which generates heat by application of electricity such as nichrome wire, and a lead wire 64a is drawn out from the heat generation vessel 62 while connected to the electric heating body 64. This is left to stand on the floor of the drying chamber 60, the receiving pan 61 is placed thereon, a power supply (battery or dry cell) 65 is connected to the drawn lead wire 64a, and the electric heating body 64 is heated, thereby chemically reacting the powder mixture to generate heat, thereby carrying out the postdrying. The heat generation vessel 62 can also be placed on the upper surface of the receiving pan 61 to carry out the postdrying according to need (drying from both above and under is also possible if necessary).

By using such a main drying device, the aforementioned test specimen having been predried to 30% in water content is subject to the active drying treatment by the reaction heat generated when the powder mixture of copper and sulfur is chemically reacted gradually under potassium silicate as a reaction control agent, and thus can achieve the targeted water content of 20% or less, preferably 10% or less quickly, and be provided to a to-be-measured sample for the foregoing various analytical methods such as X-ray fluorescence spectrometry, total reflection X-ray fluorescence spectrometry, etc.

Moreover, in this device, the heating source for the postdrying which makes the predried test specimen 20% or less, preferably 10% or less in water content is the reaction heat by the powder mixture of iron or copper and sulfur, and accordingly heating treatment becomes possible by carrying a simple external power supply as a heating source for reaction start, such as a battery or dry cell. Thus, electrical equipment is not required as in a conventional case where a large amount of power consumption is involved, so that drying at the collection site becomes possible.

Further, in the postdrying, one or more kinds of volatile alcohols, more specifically, alcohols and/or ketones having volatility and mixed with water at any ratio such as methyl alcohol ($CH_3OH$), ethyl alcohol ($C_2H_5OH$), n-propyl alcohol ($CH_3CH_2CH_2OH$), iso-propyl alcohol ($CH_3CH(OH)CH_3$), acetone ($CH_3COCH_3$), methyl ethyl ketone ($CH_3COC_2H_5$) are appropriately selected and added to the aforementioned predried sample. When the sample having been added with the above is stirred and provided for the postdrying according to need, water is vaporized while promoted by volatilization of the added alcohols and/or ketones, thereby allowing a postdrying time to be reduced. Although the reduction time varies in heating temperature, kind and added amount of alcohol and/or ketone, etc., a reduction of approximately 30% at maximum is possible as compared with a case where a volatile alcohol and/or ketone is not added. Accordingly, making the water content of the sample 20% or less, preferably 10% or less is further sped up, thereupon improving workability.

It is a matter of course that the present invention is not restricted to the above embodiments. When an analytical sample is dried, an object to be dried other than water includes an organic matter, further, an easily vaporized element such as mercury, arsenic, antimony, cadmium, etc., a simple substance of a compound, or a mixture of the above easily vaporized substances. These easily vaporized substances can be removed efficiently and provided as an analytical sample in the same manner.

The sample of residual components thus dried can be used as a sample for infrared spectroscopy, atomic absorption spectrometry, emission spectrometry, gas chromatographic spectrometry, and gravimetric analysis without being restricted to X-ray fluorescence spectrometry or total reflection X-ray fluorescence spectrometry, as described above. Further, a component having been vaporized by the foregoing drying treatment can also be provided as a sample for analysis by trapping and the like. Such a residual component and a vaporized component can both be used as an analytical sample.

INDUSTRIAL APPLICABILITY

The present invention is capable of early and efficiently drying an analytical sample used in various chemical analyses such as X-ray fluorescence spectrometry, total reflection X-ray fluorescence spectrometry, infrared spectroscopy, atomic absorption spectrometry, emission spectrometry, gas chromatographic spectrometry, gravimetric analysis, etc., and thus, such industrial application becomes possible.

What is claimed is:

1. A method for drying a soil sample, the method comprising:
    packing the soil sample onto an absorbent polymer, the absorbent polymer having been placed within a container before the packing; and
    drying the packed soil sample.

2. The method of claim 1, wherein the soil sample has a water content of 30% or more before drying, the water content of the soil sample corresponding to a weight of water in the soil sample relative to a total weight of the soil sample.

3. A method for drying a soil sample, the method comprising:
    predrying a packed soil sample using an absorbent polymer, the absorbent polymer having been placed within a container before the predrying;
    removing the predried soil sample from the container, and postdrying the removed soil sample by heating the removed soil sample with a heat source until a water content of the postdried soil sample is 20% or less, the water content of the postdried soil sample corresponding to a weight of water in the postdried soil sample relative to a total weight of the soil sample.

4. The method of claim 3, wherein the heat source for the postdrying is an electrothermal heater.

5. The method of claim 3, wherein the heat source for the postdrying is obtained by condensing light having been emitted from a lamp body by a convex lens.

6. The method of claim 3, wherein the heat source for the postdrying is a flame for burning a combustible fuel.

7. The method of claim 3, wherein the heat source for the postdrying is a drier with a built-in dry cell.

8. The method of claim 3, wherein the heat source for the postdrying is heat generated when calcium oxide or barium oxide is reacted with water.

9. The method of claim 3, wherein the heat source for the postdrying is heat generated when concentrated sulfuric acid is diluted with water.

10. The method of claim 3, wherein the heat source for the postdrying is heat generated when metal powder is oxidized.

11. The method of claim 3, wherein the heat source for the postdrying is heat generated when alkali metal hydroxide or alkaline earth metal hydroxide is bonded with water and hydrated.

12. The method of claim 3, wherein the heat source for the postdrying is heat generated when a vaporized petroleum combustible is burned in the presence of a catalyst of platinum cotton.

13. The method of claim 3, wherein the heat source for the postdrying is heat generated when charcoal powder of plants having been hardened by kneading is burned.

14. The method of claim 3, wherein the heat source for the postdrying is heat generated by the reaction of a mixture of iron or copper powder and sulfur powder.

15. The method of claim 3, wherein the removed soil sample is postdried with a volatile alcohol and/or a ketone.

16. The method of claim 1, wherein at least one of a residual component or a vaporized component that results from the drying is used in an analysis of the soil sample.

17. A system for drying a soil sample, the apparatus comprising:
a predrying device comprised of:
a container; and
an absorbent polymer inside of the container;
wherein the soil sample, once placed in the container, is located on an upper surface of the absorbent polymer, and
wherein the predrying device is capable of drying the soil sample until a predried soil sample has a water content of 30% or less after predrying, the water content of the predried soil sample corresponding to a weight of water in the predried soil sample relative to a total weight of the soil sample; and
a postdrying device that is capable of further drying the predried soil sample until a postdried soil sample has a water content of 20% or less after postdrying using a heat source, the water content of the postdried soil sample corresponding to a weight of water in the postdried soil sample relative to a total weight of the soil sample.

* * * * *